United States Patent [19]
Leist et al.

[11] 4,359,054
[45] Nov. 16, 1982

[54] RETAINER ARRANGEMENT AND METHOD FOR APPLYING A MEMBRANE TO A PHYSIOLOGICAL SENSING UNIT

[75] Inventors: Helmut J. Leist; Karl-Heinz Pomorin, both of Freiburg im Breisgau, Fed. Rep. of Germany

[73] Assignee: Hellige GmbH, Freiburg im Breisgau, Fed. Rep. of Germany

[21] Appl. No.: 276,184

[22] Filed: Jun. 22, 1981

[30] Foreign Application Priority Data

Jul. 4, 1980 [DE] Fed. Rep. of Germany ....... 3025409

[51] Int. Cl.$^3$ .............................................. A61B 5/00
[52] U.S. Cl. .................................. 128/635; 128/640; 204/195 B; 204/195 P
[58] Field of Search ...................... 128/635, 632, 640; 204/195 P, 195 B

[56] References Cited

U.S. PATENT DOCUMENTS 4,273,134  6/1981  Ricciardelli ..................... 128/635

Primary Examiner—Kyle L. Howell
Assistant Examiner—Daniel P. Burke

[57] ABSTRACT

Disclosed herein are a method and a retainer arrangement for applying a membrane to a physiological sensing unit for the transcutaneous determination of the magnitude of physiological quantities, particularly for measuring the partial pressure of gases in blood or the like. The invention proposes the preparation of a preassembly thus constituting a spare part which will be ready for application to the sensing unit when needed. The preassembly comprises a membrane, a clamping ring for removably assembling the membrane with the sensing unit, and means, including an auxiliary retainer element, for temporarily and removably securing the membrane to the clamping ring prior to assembly with the sensing unit.

8 Claims, 2 Drawing Figures

RETAINER ARRANGEMENT AND METHOD FOR APPLYING A MEMBRANE TO A PHYSIOLOGICAL SENSING UNIT

FIELD OF THE INVENTION

The invention relates to physiological sensing units for the transcutaneous determination of the concentration of substances, particularly the partial pressure of gases, such as $O_2$ and $CO_2$, within blood and within body tissue, and it is particularly concerned with a retainer arrangement for the measuring surface membrane of such sensing unit.

DESCRIPTION OF THE PRIOR ART

Physiological sensing units for the transcutaneous determination of the partial pressure of gases within blood or within body tissue employ, for the purpose of performing the measuring step, one or several electrodes and a counterelectrode embedded within a measuring surface. Prior to the measuring step, a user of the device must polish the electrodes and the counterelectrode, whenever necessary. They must then be coated with an electrolyte and covered with a membrane. These preparatory steps must be repeated whenever the physiological sensing unit is intended to be used for performing a measuring step on a different individual or whenever the unit is to be used over extended periods of time, such as one week or longer, in connection with the same individual. In the course of clinical routine operation, it is important that these preparations can be attended to without excessive loss of time and still with high reliability.

In an earlier development of physiological sensing units of the type described above, a clamping ring is used for mounting the membrane to the measuring surface of the unit. The clamping ring is secured to the sensing unit by means of a threaded ring which surrounds the clamping ring. When preparing the sensing unit for use, the round membrane must firstly be aligned with the round measuring surface of the sensing unit in a concentric manner. Subsequently, the membrane must be secured in its working position by means of the clamping ring and, finally, the clamping ring must, in turn, be secured in its position by the threaded ring. Applying the membrane to the sensing unit therefore requires several sequential steps whose performance can lead to difficulties and loss of time, particularly when unskilled personnel is employed in a clinical routine environment.

Consequently, there exists a need for a possibility of securing the membrane to the measuring surface of a physiological sensing unit by simplified manipulations.

As will become better understood from the following description of a specific embodiment, the invention is seen in the provision of a retainer arrangement for applying a membrane to a physiological sensing unit for the transcutaneous determination of the magnitude of physiological quantities, particularly for measuring the partial pressure of gases in blood or the like, wherein the retainer arrangement comprises a membrane, a clamping ring for removably assembling the membrane with the sensing unit, and means, including an auxiliary retainer element, for temporarily and removably securing the membrane to the clamping ring prior to assembly with the sensing unit.

In accordance with one of the basic concepts, the invention starts out from the thought of providing preassemblies constituting spare parts, each in the form of a combination of a membrane for the sensing unit with a retainer ring for removably mounting the membrane to the sensing unit, with such preassemblies being adapted for use as the retainer arrangement for applying a membrane to a physiological sensing unit for the transcutaneous determination of the magnitude of physiological quantities, particularly for measuring the partial pressure of gases in blood or the like.

In still somewhat different terms, the invention is susceptible of presentation as a method, namely a method for applying a membrane to a physiological sensing unit for the transcutaneous determination of the magnitude of physiological quantities, particularly for measuring the partial pressure of gases in blood or the like, wherein the membrane is removably secured to the sensing unit in its working position by means of a clamping ring, the method comprising the steps of preassembling the membrane with the clamping ring by means of an auxiliary retainer element, applying the preassembly thus formed to the sensing unit with each, the clamping ring and the membrane, in its working position, and removing the auxiliary retainer element.

An important advantage of the invention resides in the fact that the user of the physiological sensing unit need not align one with the others the various parts, namely the membrane, the clamping ring and the housing of the unit, during the preparatory steps. Rather, it is merely necessary to apply the clamping ring with the membrane already secured to it as a prefabricated preassembly to the otherwise prepared sensing unit and, subsequent to this step of application, the loosely adhered auxiliary retainer element, which is suitably a disc of self-adhesive foam material, can be removed.

In accordance with one embodiment of the invention, the contact surface of the housing of the unit, which cooperates with an internal circumferential collar of the clamping ring, is almost cylindrical and the collar of the clamping ring is slightly conically shaped. This feature leads to satisfactory mounting conditions for the membrane.

In order to permit easy exchange of the membrane together with the clamping ring, the exterior circumference of the clamping ring may be provided with a short protrusion or tongue integrally formed with the ring to form a handle by means of which a circumferential rim of the clamping ring, which is preferably made of resilient plastic such as polyethylene, can be caused to snap into a circular groove in the external circumference of the housing of the sensing unit or by which it can be removed from the groove. In accordance with an alternative, instead of the mentioned handle or tongue, a slightly protruding external rim of the clamping ring may be provided.

Uniform tension of the membrane, as well as the uniform distribution of the thin electrolyte layer disposed below the membrane, may be achieved by the feature that the contact surface of the clamping ring exhibits slight convex shape with respect to the basic body portion, i.e. the housing of the sensing unit, in order to urge the clamping ring undisplaceably against the contact surface, even after the foam material serving as the auxilairy retainer element has been removed.

The foam material disc, which is easily removably applied, due to its self-adhesive properties, to the external surface of the membrane, has its shape and thickness preferably selected such that it fits into the ring-shaped inner space of the clamping ring, so that, during manufacturing the retainer arrangement of the invention, the membrane and therewith the foam material disc are already perfectly accurately centered with respect to the clamping ring. It can thus be seen that the preassembly of the clamping ring, the membrane and the foam material disc, which adheres to the external surface of the membrane and fits into the ring space of the clamping ring, can be made available as a spare part or element, ready for application to the sensing unit, thereby to permit an easy exchange of the membrane.

A significant improvement results from the various aspects and features of the invention, because, when exchanging the membrane upon physiological sensing units, any awkward and time-consuming centering step in connection with the membranes, heretofore supplied as separate elements, is avoided. The membrane can be exchanged rapidly and readily, without any need to contact the membrane with the fingers. Moreover, the user of the device need no longer be concerned about adequate tension of the membrane and about uniform distribution of the electrolyte underneath the membrane. After having cleaned the measuring surface and, if necessary, subsequent to the application of drops of electrolyte, the user merely mounts, by the application of pressure, the membrane to the measuring surface and then removes the auxiliary retainer element, such as the foam material disc, from the exterior side of the membrane. This can be done easily because the disc only loosely adheres to that surface and, at this point in time, protrudes therefrom.

BRIEF DESCRIPTION OF THE DRAWINGS

The invention and advantageous details will become better understood from the following description of an exemplary embodiment illustrated in the drawing, in which.

In the figures of the drawing, mutually corresponding elements are identified by use of the same reference characters.

DETAILED DESCRIPTION OF A PREFERRED EMBODIMENT

Figure 1:
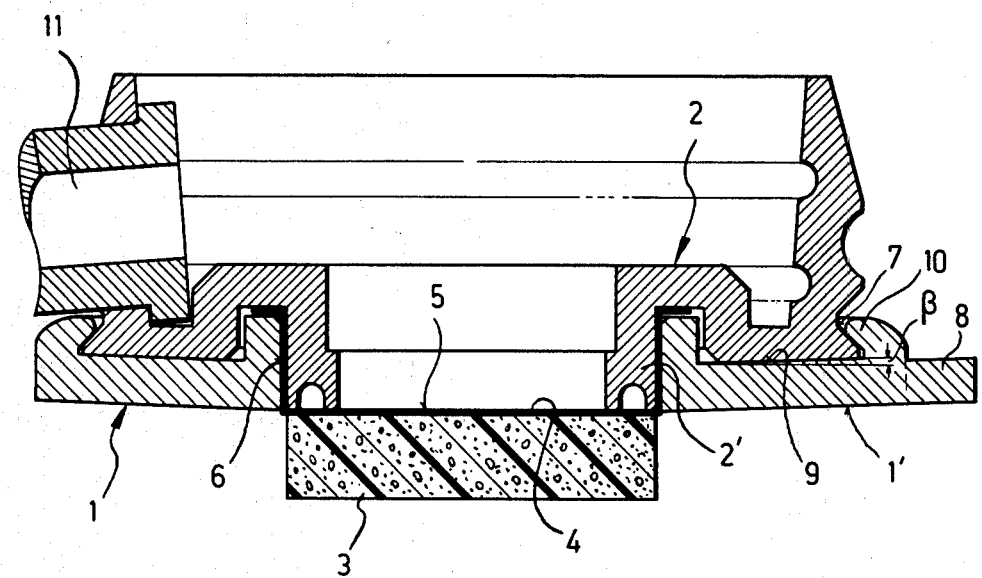
FIG. 1 is a sectional view through the housing of a physiological unit having a clamping ring assembled therewith, together with a membrane and a foam material disc adhering thereto, prior to its removal.

FIG. 1 illustrates a housing 2 of a physiological sensing unit of the type frequently referred to as a polarographic sensing unit, having a lateral extension which accommodates a signal cable 11. The internal components of the unit (not shown) may be of conventional construction and therefore need not be further described herein. The measuring surface 5, positioned within the opening of a downwardly slightly protruding peripheral cylindrical rim 2' of the housing 2, is covered by a circular membrane 4, made of thin foil and applied under tension. The membrane surface that faces away from the sensing unit has applied to it a circular foam material portion 3 which is preferably of the self-adhesive type. Diameter and height of the foam material portion 3 are preferably selected such that it is a disc that accurately fits into the circular recess, i.e. ring space, of a clamping ring 1. An interior collar of the clamping ring 1 maintains the membrane 4 in its working position. The ring space accommodates the removable foam material disc before its removal which will occur once the membrane will have been applied to the sensing unit (see FIG. 2). Thus, the foam material disc 3 adheres to the membrane as a protective cover only until a user removes it after the membrane has been pulled over the pickup device. As the foam material portion or disc 3 is accommodated with the clamping ring 1, it retains the membrane 4 loosely against the clamping ring 1, as long as the clamping ring 1 and the membrane 4 have not yet been assembled with the sending unit.

As a result of the condition that the membrane is concentrically assembled with the clamping ring 1 by means of the foam material disc 3, the membrane 4 is concentrically positioned with respect to the ring space in the clamping ring 1 and, therefore, it is concentrically applied to the measuring surface 5, once the clamping ring 1 has been mounted to the sensing unit. Advantageously, the otherwise cylindrical contact surface 6 of the collar portion of the clamping ring 1 is shaped to exhibit a slightly conical geometry which tapers from the measuring surface 5, so that the collar portion of the clamping ring 1 which faces the cylindrical portion 2' of the housing 2 can be slightly elastically deformed, thereby to put the membrane 4 under tension when sliding the clamping ring 1 upon the housing 2 of the sensing unit. This feature contributes to a satisfactory clamping effect and causes appreciable tension of the membrane. The foam material disc 3, as the result of uniform pressure which it applies to the membrane 4 during the step of mounting the clamping ring 1 and the membrane 4 to the sensing unit, causes uniform distribution and adjustment of the thickness of the layer of the electrolyte which had previously been applied to the measuring surface 5.

The normally round foam material disc 3 thus retains the membrane 4 in a central position upon the clamping ring 1 prior to application to the sensing unit. Simultaneously, it serves as a protective cover for the membrane, inasmuch as the membrane should be prevented from contact with the fingers during the application to the sensing unit.

As illustrated in the drawings, the clamping ring 1 may be provided with a slightly inwardly bent retaining ring 10 extending along its outer periphery, which ring 10 snaps into and is received in a circular peripheral groove 7 of the housing 2, thereby to secure the clamping ring in its position. The outer rim of the clamping ring 1 may be provided with a handle-type protrusion or tongue 8, by which the clamping ring can be grasped and easily pulled off, whenever the membrane must be changed. The tongue or handle 8 can be replaced by a slightly protruding circumferential rim (not shown).

Figure 2:
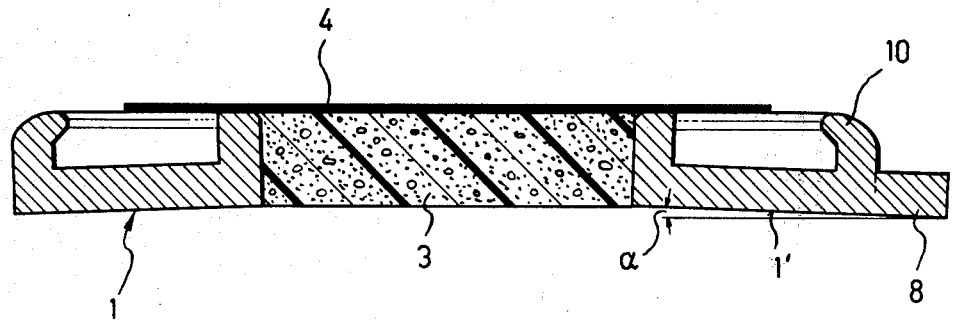
FIG. 2 is a sectional view through the preassembly of a clamping ring with a membrane and with the foam material disc adhered thereto, thus constituting a spare part, prior to application of the membrane to the sensing unit.

FIG. 2 illustrates the clamping ring 1 when forming part of a prefabricated spare part constituting a preassembly. As shown, the foam material portion or disc 3 fills the ring space of the clamping ring and serves as a temporary retaining element, as well as a protective cover for the membrane 4, due to the presence of a layer of adhesive material on its upper surface. As illustrated in the drawing in exaggerated proportions, the ring flange surface 1' of the clamping ring 1 assumes an orientation in which it is inclined from the center towards the periphery at an angle $\alpha$, so that contact pressure along the surface 9 will develop when the retaining ring 10 will be received in the circumferential groove 7. The angle α may be of a magnitude within the range of 1 to 5 angular degrees.

FIG. 1 illustrates the physiological sensing unit with the preassembly of the clamping ring 1 and the membrane 4 applied to the measuring surface 5, but prior to removal of the foam material disc 3. The clamping ring 1 retains the membrane 4 by pressure applied along the contact surface 6 and secures the membrane to the measuring surface 5 of the physiological sensing unit. By means of the application of two adhesive layers to the foam material portion 3, one at each major surface, the disc 3 can be secured to a dispensing, i.e. removing, arrangement (not illustrated) which cooperates with its lower surface which faces away from the membrane 4. Such arrangement facilitates removal of the foam material disc 3 from the membrane 4 once it has been applied, which feature prevents manual contact with the membrane.

As a further improvement and for increasing the clamping effect between the conical contact surface 6 of the collar-shaped portion of the clamping ring, the contact surface 9 which cooperates with the ring flange surface 1' of the clamping ring 1, can be inclined from the center to the periphery to assume an orientation to form an angle β of 2 to 6 angular degrees, preferably about 4 angular degrees.

Upon termination of a measuring step and during the preparation of the next measuring step, the clamping ring 1 is removed from the housing 2 of the sensing unit which is done by grasping the clamping ring 1 by means of the ring-shaped rim, or the handle 8, and by pulling it away from the housing 2 of the physiological sensing unit by simple movement of the handle.

It is to be noted that many modifications can be made by substitutions or additions, under use of equivalents for features disclosed herein, with such changes falling within the scope of the invention as defined by the appended claims.

We claim:

1. A retainer arrangement for applying a membrane to a physiological sensing unit for the transcutaneous determination of the magnitude of physiological quantities, particularly for measuring the partial pressure of gases in blood or the like, comprising a membrane, a clamping ring for removably assembling the membrane with the sensing unit, and means, including an auxiliary retainer element made of self-adhesive foam material, for temporarily and removably securing the membrane to the clamping ring prior to assembly with the sensing unit.

2. Retainer arrangement according to claim 1, wherein the auxiliary retainer element has the shape of a disc which fits into an opening in the clamping ring.

3. Retainer arrangement according to claim 1, wherein the disc exhibits adhesive properties at each of its two major surfaces.

4. Retainer arrangement according to claim 1, or claim 2, wherein the clamping ring is provided with a circumferentially protruding, inwardly oriented rim which resiliently fits and removably snaps into a peripheral groove of the sensing unit.

5. Retainer arrangement according to claim 1, or claim 2, wherein the clamping ring has an internally facing surface which is slightly conically shaped to taper in the direction toward the sensing unit, the surface of the sensing unit which clamps the membrane against the conical surface being substantially cylindrical.

6. Retainer arrangement according to claim 1, or claim 2, comprising at least one portion of the clamping ring which protrudes from its circumference to form a handle.

7. Retainer arrangement according to claim 1, or claim 2, wherein the surface of the clamping ring which, upon assembly, makes contact with a front surface of the sensing unit is slightly inclined to approach the membrane from the circumference toward the center of the clamping ring prior to assembly.

8. A method for applying a membrane to a physiological sensing unit for the transcutaneous determination of the magnitude of physiological quantities, particularly for measuring the partial pressure of gases in blood or the like, wherein the membrane is removably secured to the sensing unit in its working position by means of a clamping ring, comprising preassembling the membrane with the clamping ring by adhering an auxiliary retainer element in the form of a disc-shaped piece of self-adhesive foam material to the membrane and fitting the disc-shaped piece into a correspondingly shaped opening in the clamping ring, means of an auxiliary retainer element, applying the preassembly thus formed to the sensing unit with each, the clamping ring and the membrane, in its working position, and removing the auxiliary retainer element.

* * * * *